(12) United States Patent
Thangaraju et al.

(10) Patent No.: US 10,500,333 B2
(45) Date of Patent: Dec. 10, 2019

(54) SYSTEM AND METHOD FOR DETERMINING AN INJECTABLE AMOUNT OF BILE REQUIRED AFTER GALLBLADDER REMOVAL SURGERY

(71) Applicant: HCL Technologies Limited, Noida, Uttar Pradesh (IN)

(72) Inventors: Shyam Thangaraju, Tamil Nadu (IN); Siva Sakthivel Sadasivam, Tamil Nadu (IN); Vishal Chaudhary, Uttar Pradesh (IN)

(73) Assignee: HCL Technologies Limited, Noida, Uttar Pradesh (IN)

( * ) Notice: Subject to any disclaimer, the term of this patent is extended or adjusted under 35 U.S.C. 154(b) by 858 days.

(21) Appl. No.: 14/975,663

(22) Filed: Dec. 18, 2015

(65) Prior Publication Data

US 2016/0213836 A1 Jul. 28, 2016

(30) Foreign Application Priority Data

Jan. 27, 2015 (IN) .............................. 227/DEL/2015

(51) Int. Cl.
*A61M 5/142* (2006.01)
*G06F 19/00* (2018.01)
(Continued)

(52) U.S. Cl.
CPC ..... *A61M 5/14276* (2013.01); *G06F 19/3462* (2013.01); *G16H 20/17* (2018.01);
(Continued)

(58) Field of Classification Search
None
See application file for complete search history.

(56) References Cited

U.S. PATENT DOCUMENTS

| 9,037,244 | B2 | 5/2015 | Sharma | |
|---|---|---|---|---|
| 2005/0277912 | A1* | 12/2005 | John | G06F 19/00 |
| | | | | 604/890.1 |

FOREIGN PATENT DOCUMENTS

| CN | 103480049 | 1/2014 |
|---|---|---|
| WO | 2013/068752 | 5/2013 |

OTHER PUBLICATIONS

John Y. L. Chiang, Bile Acid Regulation of Gene Expression: Roles of Nuclear Hormone Receptors, Endocrine Reviews, 443-463, 23(4), The Endocrine Society, USA.

* cited by examiner

*Primary Examiner* — Olivia M. Wise
(74) *Attorney, Agent, or Firm* — Knobbe, Martens, Olson & Bear, LLP

(57) ABSTRACT

Disclosed is a system and a method for determining an injectable amount of bile required for a patient after gallbladder removal. The system comprises a receiving module, a creating module, and a determining module. The receiving module may receive a bile-flow rate, physiological parameters of a patient, and amount of fatty food in an alimentary tract of the patient. Based on these data received, the creating module may create a graph. Further, the determining module may determine a correlation between the bile-flow rate and the amount of fatty food in the alimentary tract based on the graph created. The correlation may be determined corresponding to a normal person and the patient which may be seen by two separate curves on the graph. Further, the determining module may determine an injectable amount of bile required for the patient based on the correlation.

11 Claims, 8 Drawing Sheets

(51) Int. Cl.
*G16H 20/17* (2018.01)
*A61M 5/172* (2006.01)
(52) U.S. Cl.
CPC .............. *A61M 2005/14208* (2013.01); *A61M 2005/1726* (2013.01); *A61M 2202/0403* (2013.01); *A61M 2205/04* (2013.01); *A61M 2205/3303* (2013.01); *A61M 2205/3334* (2013.01); *A61M 2205/50* (2013.01); *A61M 2210/1075* (2013.01); *A61M 2230/00* (2013.01)

SYSTEM AND METHOD FOR DETERMINING AN INJECTABLE AMOUNT OF BILE REQUIRED AFTER GALLBLADDER REMOVAL SURGERY

CROSS-REFERENCE TO RELATED APPLICATIONS AND PRIORITY

The present application claims benefit from Indian Complete Patent Application No. 227/DEL/2015, filed on Jan. 27, 2015, the entirety of which is hereby incorporated by reference.

TECHNICAL FIELD

The present subject matter described herein, in general, relates to a method and a system for determining an injectable amount of bile required for a patient after gallbladder removal.

BACKGROUND

Organ removal from a person's body for various treatment purposes is a common practice in a medical field. The organ removal is done for different reasons like malignant tumors (cancerous growths), benign tumors (non cancerous growths), infection, gangrene formation, trauma/injuries, organ donation and the like. The organ like gallbladder may also be surgically removed for reasons like gallstones which are small hard masses of cholesterol and bile salts formed in the gallbladder. The formation of the gallstones causes various problems like blocking flow of bile out of the gallbladder, swelling, abdominal pain, vomiting, indigestion and many other problems. For treating such bodily problems, gallbladder removal surgery is commonly performed by doctors/practitioners.

The function of the gallbladder is to store the bile secreted by liver and pump it if there is fatty food in the intestine. The bile is a digestive liquid required for dissolving the fatty food in the intestine. Thus, for maintaining digestive balance in the person's body, the delivery of the bile into the intestine is constantly required. But, when the gallbladder is removed, the person's body usually doesn't compensate for some time and in many cases never reaches the pre-removal stage due to the lack of timing of bile delivery (i.e., the bile will just flow from the liver to the intestine). Removal of the gallbladder means the removal of a reservoir which stores the bile and maintains the flow of the bile into the intestine based on the amount of fatty food present in the intestine. After the gallbladder removal, the flow of the bile gets disturbed and affects the digestive system of the person's body. Even if a provision is made to deliver the bile externally into the person's body, determining an exact amount of bile required to be delivered becomes another challenge for the doctors. Thus, there is a lack of solution which could model these components (liver, gallbladder, bile etc) and could appropriately guide the doctor for providing post-operative compensation after the gallbladder removal.

SUMMARY

This summary is provided to introduce aspects related to systems and methods for determining an injectable amount of bile required for a patient after gallbladder removal are further described below in the detailed description. This summary is not intended to identify essential features of subject matter nor is it intended for use in determining or limiting the scope of the subject matter.

In one implementation, a system for determining an injectable amount of bile required for a patient after gallbladder removal is disclosed. The system comprises a processor and a memory coupled to the processor for executing a plurality of modules stored in the memory. The plurality of modules comprises a receiving module, a creating module, and a determining module. The receiving module may receive a bile-flow rate, physiological parameters of a patient, and amount of fatty food in an alimentary tract of the patient. The bile-flow rate may indicate a first amount of bile delivered from the gallbladder to the alimentary tract prior to the gallbladder removal. Further, the physiological parameters may comprise age, sex, race, ethnicity, height, and weight of the patient. Further, the creating module may create a graph based on the bile-flow rate, the physiological parameters, and the amount of fatty food in the alimentary tract. Further, the determining module may determine a correlation between the bile-flow rate and the amount of fatty food in the alimentary tract. The determining module may further determine the injectable amount of the bile required for the patient based on the correlation determined.

In another implementation, a method for determining an injectable amount of bile required for a patient after gallbladder removal is disclosed. The method may comprise receiving, by a processor, a bile-flow rate, physiological parameters of a patient, and amount of fatty food in an alimentary tract of the patient. The bile-flow rate may indicate a first amount of bile delivered from the gallbladder to the alimentary tract prior to the gallbladder removal. Further, the physiological parameters may comprise age, sex, race, ethnicity, height, and weight of the patient. The method may further comprise creating, by the processor, a graph based on the bile-flow rate, the physiological parameters, and the amount of fatty food in the alimentary tract. Further, the method may comprise determining, by the processor, a correlation between the bile-flow rate and the amount of fatty food in the alimentary tract. The method may further comprise determining, by the processor, an injectable amount of bile required for the patient based on the correlation determined.

Yet in another implementation a non-transitory computer readable medium embodying a program executable in a computing device for determining an injectable amount of bile required for a patient after gallbladder removal is disclosed. The program may comprise a program code for receiving a bile-flow rate, physiological parameters of a patient, and amount of fatty food in an alimentary tract of the patient. The bile-flow rate may indicate a first amount of bile delivered from the gallbladder to the alimentary tract prior to the gallbladder removal. Further, the physiological parameters may comprise age, sex, race, ethnicity, height, and weight of the patient. Further, the program may comprise a program code for creating a graph based on the bile-flow rate, the physiological parameters, and the amount of fatty food in the alimentary tract. The program may further comprise a program code for determining a correlation between the bile-flow rate and the amount of fatty food in the alimentary tract. Further, the program may comprise a program code for determining an injectable amount of bile required for the patient based on the correlation determined.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Systems and methods for determining an injectable amount of bile required for a patient after gallbladder removal are described. The present disclosure models different components (liver, gallbladder, bile, food etc) to maintain homeostasis of the body by providing post-operative compensation for maintaining imbalances in the patient's body after the gallbladder removal. The function of the gallbladder is to store bile secreted by liver and pump out the bile to an alimentary tract if the gallbladder senses fatty food present in the alimentary tract. The bodily sensors may send signals to the liver and the gallbladder to release a certain amount of bile required for digesting the fatty food. In response to the signals, the required amount of bile is secreted by the liver and further delivered by the gallbladder to the alimentary tract. But, after the removal of the gallbladder the flow of the bile required for digesting the fatty food gets disturbed which leads to abnormality in the digestive system of the patient's body.

To keep the patient's body in normal state after gallbladder removal, the present disclosure has disclosed the system and the method for determining an accurate amount of the bile to be injected into the patient's body for digesting the fatty food. The accurate amount of the bile may be determined based on different factors like amount of fatty food present in the alimentary tract and bile-flow rate of the patient in normal condition. Thus, the system provides post-operative compensation that will be needed when the gallbladder is removed to help achieve faster recovery of the patient. Further, the system may be connected with a device (an injectable device) capable for injecting the amount of the bile determined to be injected into the patient body.

While aspects of described system and method for determining the amount of bile required for a patient after gallbladder removal may be implemented in any number of different computing systems, environments, and/or configurations, the embodiments are described in the context of the following exemplary system.

Figure 1:
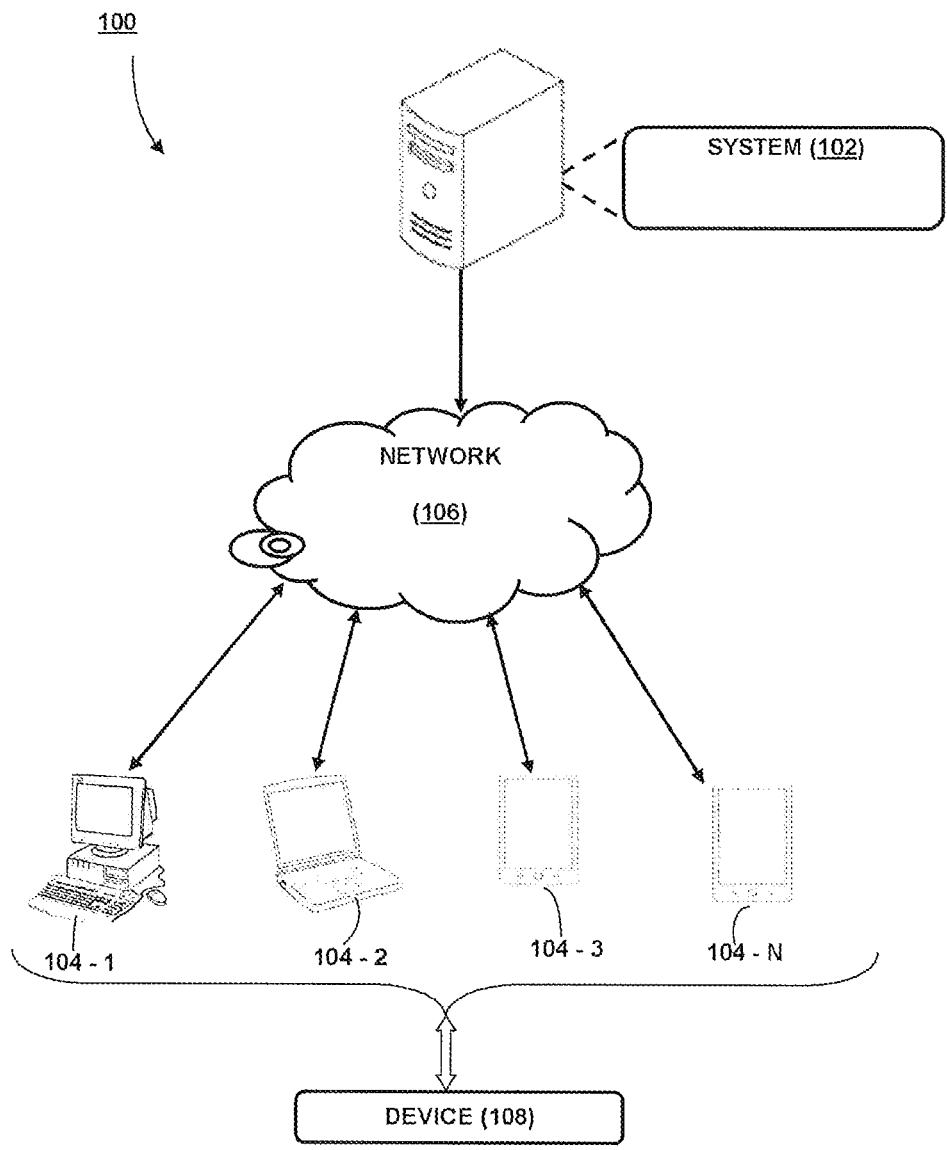
FIG. 1 illustrates a network implementation of a system for determining an injectable amount of bile required for a patient after gallbladder removal, in accordance with an embodiment of the present disclosure.

Referring to FIG. 1, a network implementation 100 of system 102 for determining an injectable amount of bile is illustrated, in accordance with an embodiment of the present subject matter. Although the present subject matter is explained considering that the system 102 is implemented for determining an injectable amount of bile on a server, it may be understood that the system 102 may also be implemented in a variety of computing systems, such as a laptop computer, a desktop computer, a notebook, a workstation, a mainframe computer, a server, a network server, a tablet, a mobile phone, and the like. In one embodiment, the system 102 may be implemented in a cloud-based environment. It will be understood that the system 102 may be accessed by multiple users through one or more user devices 104-1, 104-2 . . . 104-N, collectively referred to as user 104 hereinafter, or applications residing on the user devices 104. Examples of the user devices 104 may include, but are not limited to, a portable computer, a personal digital assistant, a handheld device, a workstation, and a medical device. The user devices 104 are communicatively coupled to the system 102 through a network 106. In one embodiment, the user devices 104 may be further connected with a device (108) capable for injecting the injectable amount of the bile determined by the system 102. In another embodiment, the system 102 may be connected with the device 108.

In one implementation, the network 106 may be a wireless network, a wired network or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further the network 106 may include a variety of network devices, including routers, bridges, servers, computing devices, storage devices, and the like.

Figure 2:
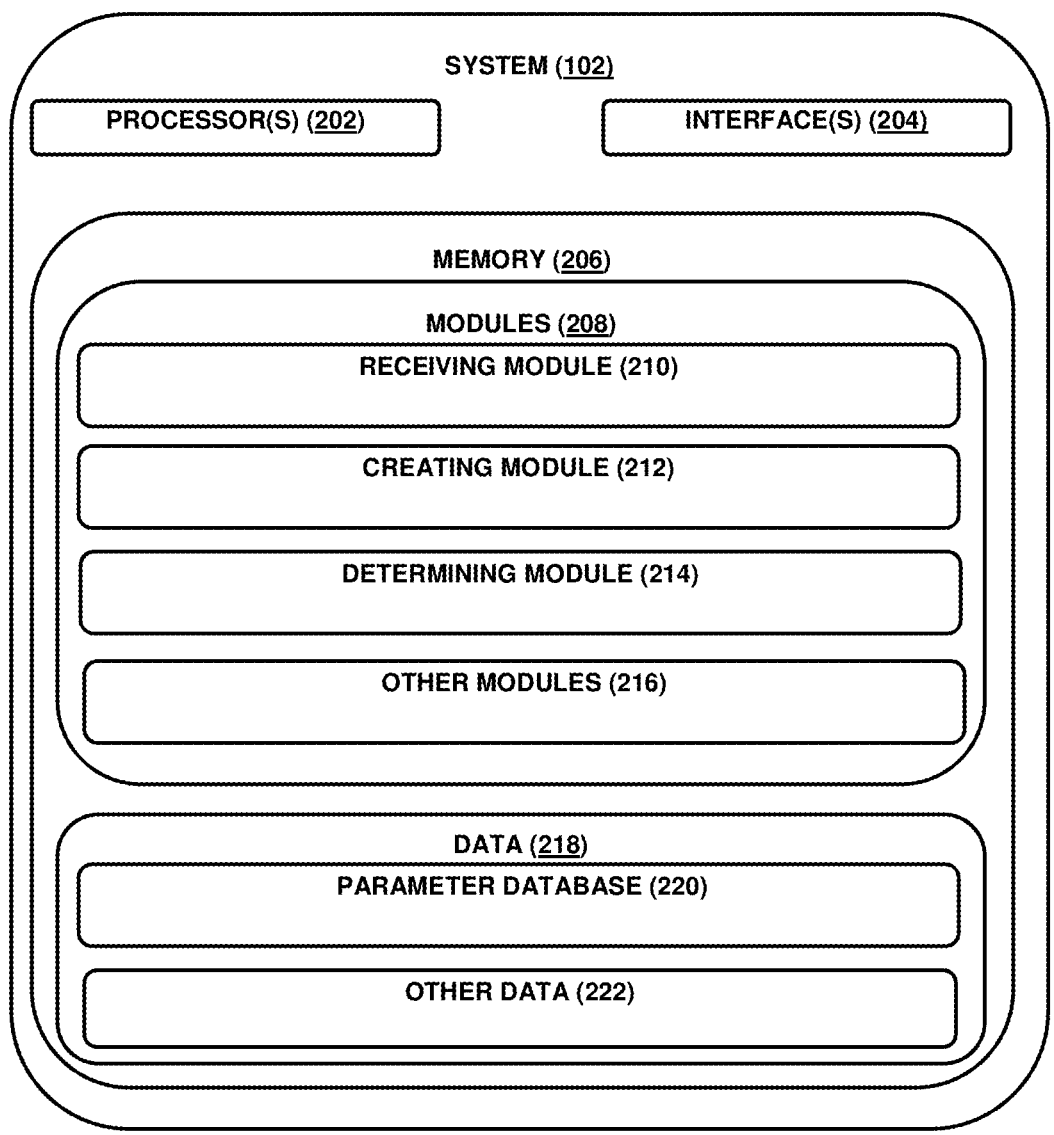
FIG. 2 illustrates the system, in accordance with an embodiment of the present disclosure.

Referring now to FIG. 2, the system 102 is illustrated in accordance with an embodiment of the present subject matter. In one embodiment, the system 102 may include at least one processor 202, an input/output (I/O) interface 204, and a memory 206. The at least one processor 202 may be implemented as one or more microprocessors, microcomputers, microcontrollers, digital signal processors, central processing units, state machines, logic circuitries, and/or any devices that manipulate signals based on operational instructions. Among other capabilities, the at least one processor 202 is configured to fetch and execute computer-readable instructions or modules stored in the memory 206.

The I/O interface 204 may include a variety of software and hardware interfaces, for example, a web interface, a graphical user interface, and the like. The I/O interface 204 may allow the system 102 to interact with a user directly or through the client devices 104. Further, the I/O interface 204 may enable the system 102 to communicate with other computing devices, such as web servers and external data servers (not shown). The I/O interface 204 can facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 206 may include any computer-readable medium or computer program product known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, a compact disks (CDs), digital versatile disc or digital video disc (DVDs) and magnetic tapes. The memory 206 may include modules 208 and data 218.

The modules 208 include routines, programs, objects, components, data structures, etc., which perform particular tasks or implement particular abstract data types. In one implementation, the modules 208 may include a receiving module 210, a creating module 212, determining module 214, and other modules 216. The other modules 216 may include programs or coded instructions that supplement applications and functions of the system 102.

The data 218, amongst other things, serves as a repository for storing data processed, received, and generated by one or more of the modules 208. The data 218 may also include a parameter database 220, and other data 222.

Figure 3A:
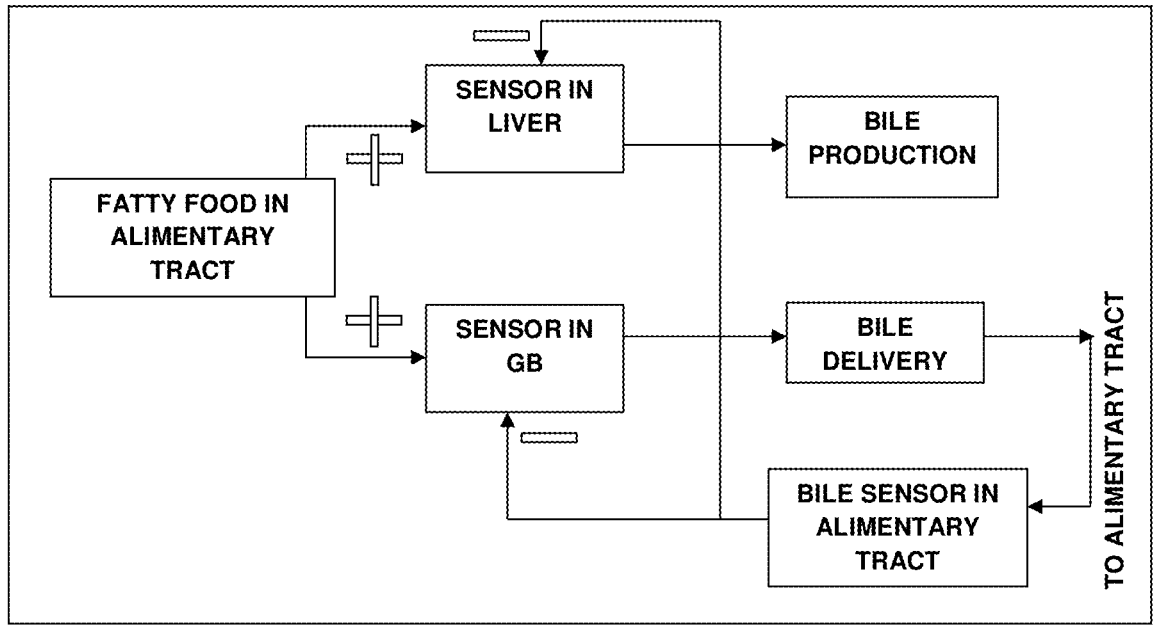
FIG. 3A-3E illustrates an example for determining the injectable amount of bile in detail, in accordance with an embodiment of the present disclosure.

Referring now to FIG. 3A-3E, illustrates an example for determining an injectable amount of bile in detail, in accordance with an embodiment of the present subject matter. The ability of the gallbladder is to pump out or deliver an amount of bile when a sensor in gallbladder senses fatty food in an alimentary tract of a patient. The sensors in the alimentary tract may send out signal to gallbladder and liver to release amount of bile from the gallbladder. The bile delivered into the alimentary tract acts as a digestive liquid for digesting the fatty food present in the alimentary tract. In general, the organ (the alimentary tract in this case) which receives the bile as an input may sends out a feedback signal about an adequacy of the bile which are then picked up by the sensors in the liver and the gallbladder (as shown in FIG. 3A). Further, it can be seen in FIG. 3A that the gall bladder receives two inputs and one output. The two inputs may include one positive feedback (stimulation) and one negative feedback (inhibition). The positive feedback indicates that the amount of fatty food present in the alimentary tract stimulate the flow of the bile from the gallbladder. Further, the negative feedback indicates that the amount of bile delivered to the alimentary tract should be held back by the gallbladder. Further, the output of the gallbladder (shown in the FIG. 3A) indicates the amount of the bile delivered from the gallbladder to the alimentary tract. Thus, for maintaining the proper bile flow, the system may attempt to formulate the output equivalent to the balance between the positive feedback and negative feedback.

Figure 3B:
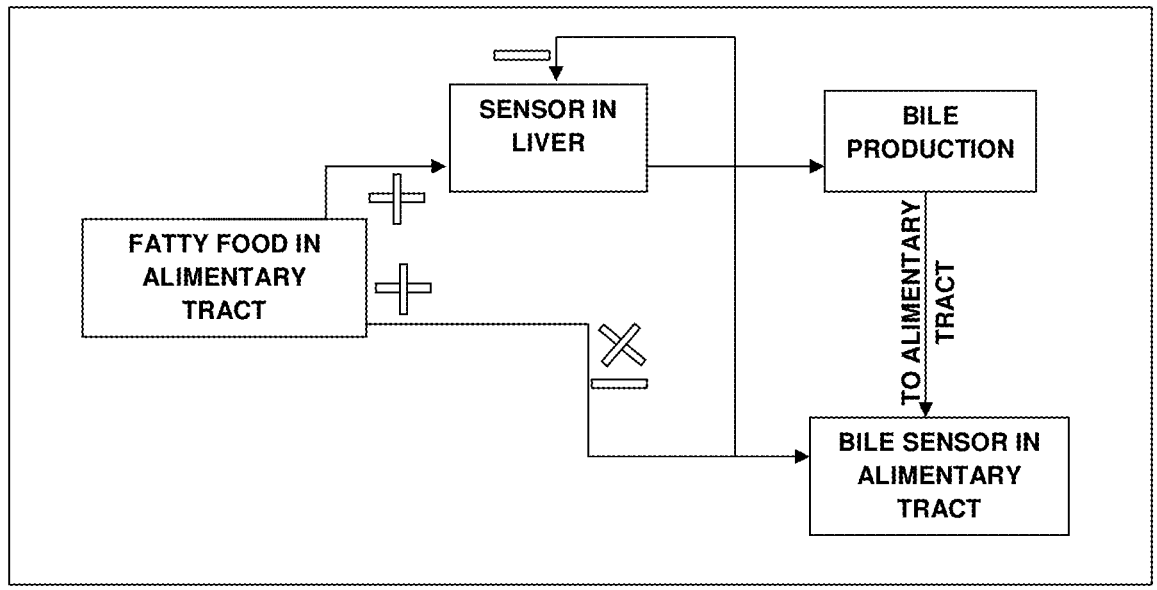

Further, based on the above details, the system models these data (positive feedback, negative feedback, amount of bile to be delivered etc) with a real-time input for compensating the patient's body after the gallbladder removal in order to bring back the patient in the normal/pre-surgical stage. According to embodiments of present disclosure, various approaches may be followed for providing compensation to the patient's body. According to an embodiment of present disclosure, one of an approach may be to match perfectly the positive feedback and the negative feedback (as shown in FIG. 3B). This may be done if a rate of flow of fatty food matches a rate of production and secretion of the bile in the liver.

Figure 3C:
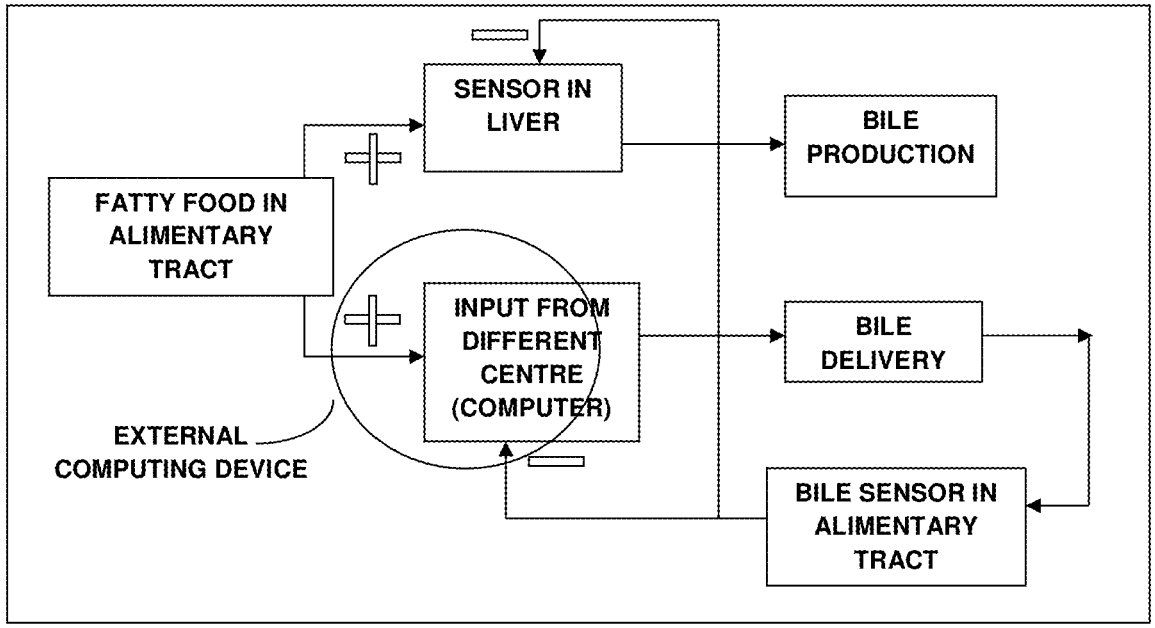

According to another embodiment of present disclosure, one of the another approach may be to reciprocate the sensors (sensor of the gallbladder) by offering similar signals from other decision making centers like external computing device (as shown in FIG. 3C). In this type of approach, the amount of bile to be delivered may be received from the external computing device.

Figure 3D:
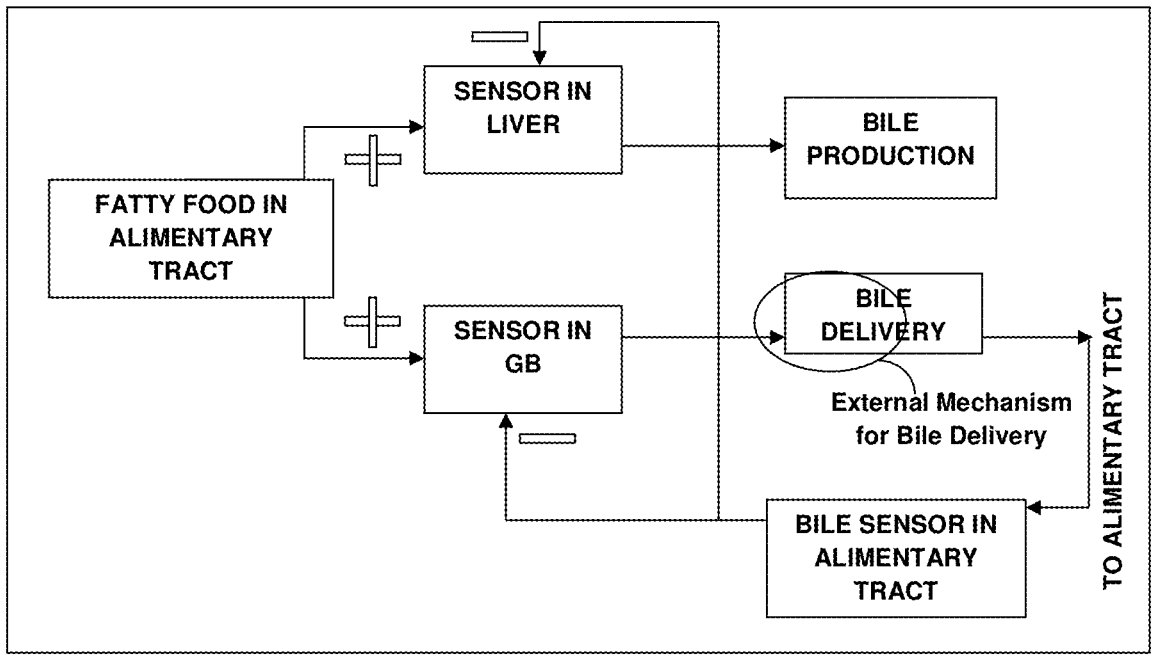

According to yet another embodiment of present disclosure, another approach may be to replace the gallbladder by an external mechanism for providing bile delivery (as shown in FIG. 3D). In all of the above approaches (3B-3D), the system attempts to compensate the gallbladder removal by providing the amount of the bile required to be injected into the patient's body. Thus, the amount of the bile required to be injected (i.e., the injectable amount) is determined by the system 102 which is explained in detail in subsequent paragraphs of the specification.

In a first step, the receiving module 210 of the system 102 may receive a bile-flow rate, physiological parameters of the patient, and an amount of food present in an alimentary tract of the patient as an input to the system 102. The bile-flow rate may indicate a first amount of bile delivered from the gallbladder to the alimentary tract prior to the gallbladder removal. Thus, the bile-flow rate provides a bile delivery pattern/information for that patient in his/her normal stage. Further, the physiological parameters may comprise age, sex, race, ethnicity, height, and weight of the patient. Further, the physiological parameters may also comprise pre-surgical data as shown in table below.

| | Ideal Person (1) | Pre Surgical Values (2) | Post Surgical Values (3) |
|---|---|---|---|
| Common hepatic duct bile flow when there is no food in the alimentary tract (A) | A1 | A2 | A3 |
| Common hepatic duct bile flow when there is food in the alimentary tract (B) | B1 | B2 | B3 |
| Common bile duct bile flow when there is no food in the alimentary tract (C) | C1 | C2 | C3 |
| Common bile duct bile flow when there is food in the alimentary tract (D) | D1 | D2 | D3 |

The above pre-surgical data may be measured on the patient using different techniques like endoscopic retrograde cholangio-pancreatography (ERCP), a computerized tomography (CT), a magnetic resonance imaging (MRI), a flow Doppler, and a radio labeling. These pre-surgical data may be measured before conducting the gallbladder removal surgery. Further, the physiological parameters along with the pre-surgical data may be stored in a parameters database 220 of the system 102. According to embodiments of present disclosure, the receiving module 210 may further receive a liver data indicating an amount of bile produced and secreted by the liver of the patient. Based on the liver data, a second amount of bile may be determined. The second amount of bile indicates a reserve amount of the bile present in biliary tract of the patient.

Further, the creating module 212 of the system 102 may create a graph based on the bile-flow rate, the physiological parameters, and the amount of fatty food in the alimentary tract. The graph may be created can be seen in FIG. 3E. Further, the determining module 214 of the system 102 may determine a correlation between the bile-flow rate and the amount of fatty food in the alimentary tract based on the graph created. Further, the graph comprises a first curve corresponding to a normal person and a second curve corresponding to the patient. The first curve and the second curve may indicate a correlation of the bile-flow rate and the amount of fatty food in the alimentary tract for the normal person the patient respectively.

Figure 3E:
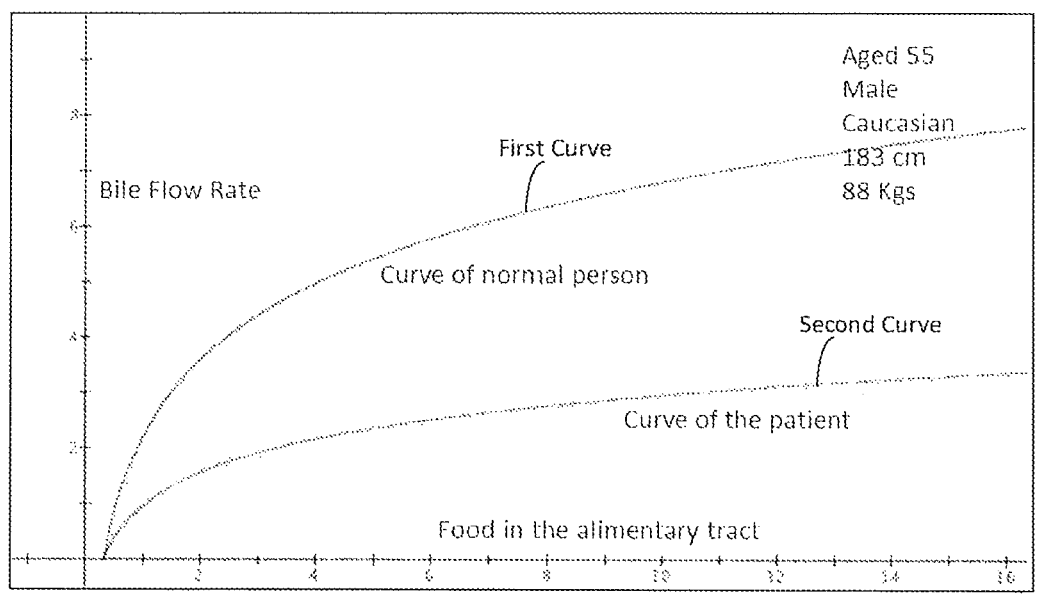

The correlation may be seen from the graph as shown in the FIG. 3E. Further, the determining module 214 of the system 102 determines the injectable amount of the bile required for the patient based on the correlation determined. Thus, the injectable amount of bile determined needs to be injected into the alimentary tract for providing the post-operative compensation to the patient's after the gallbladder removal. For injecting the injectable amount of the bile, a device 108 may be used. The device 108 and its working are explained below in detail.

Figure 4A:
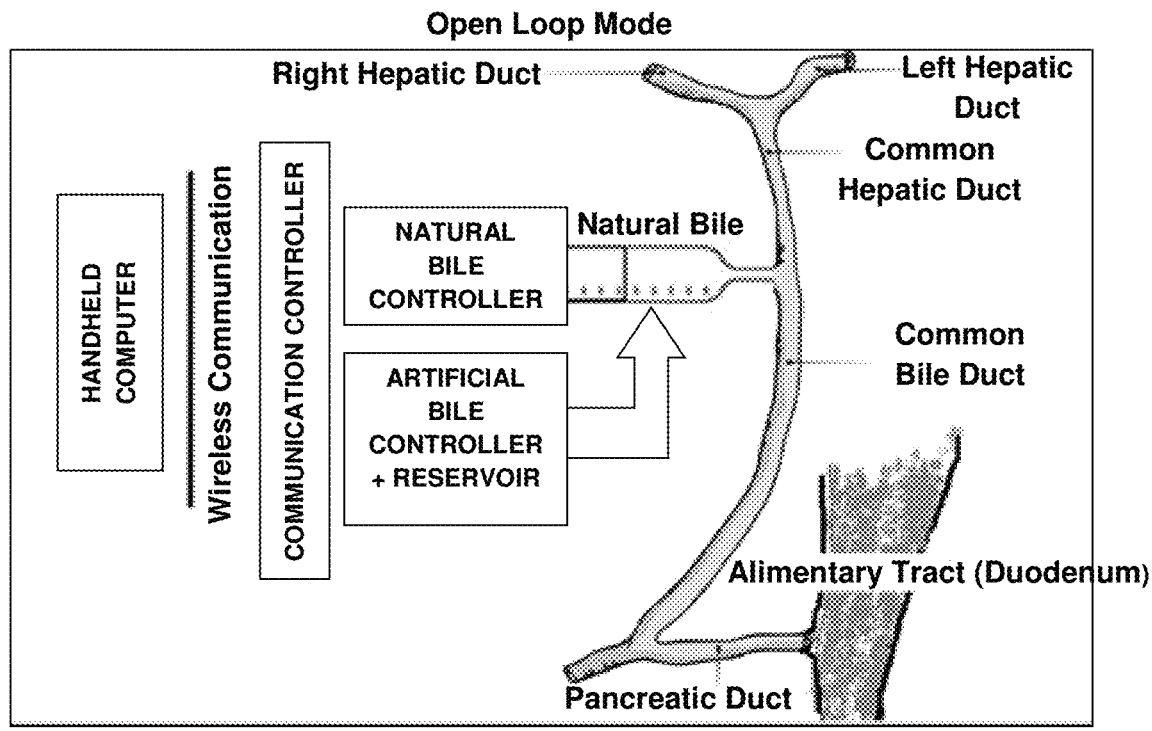
FIG. 4A-4C illustrates working a device in an open loop and close loop mode for injecting the injectable amount of the bile into the patient's body, in accordance with an embodiment of the present disclosure
Figure 4B:
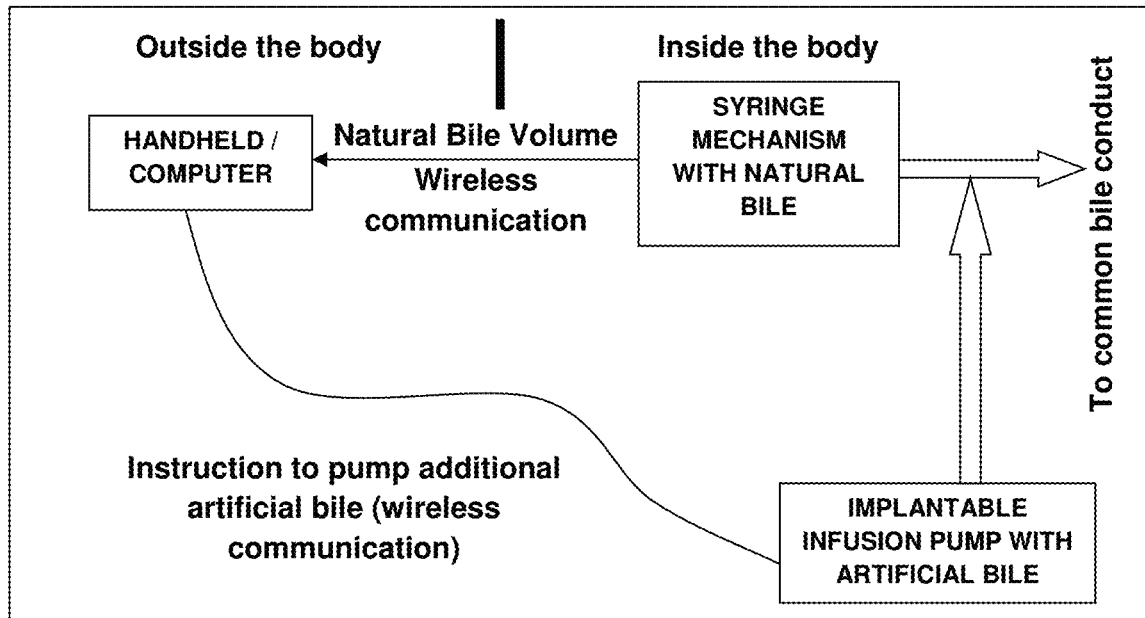
Figure 4C:
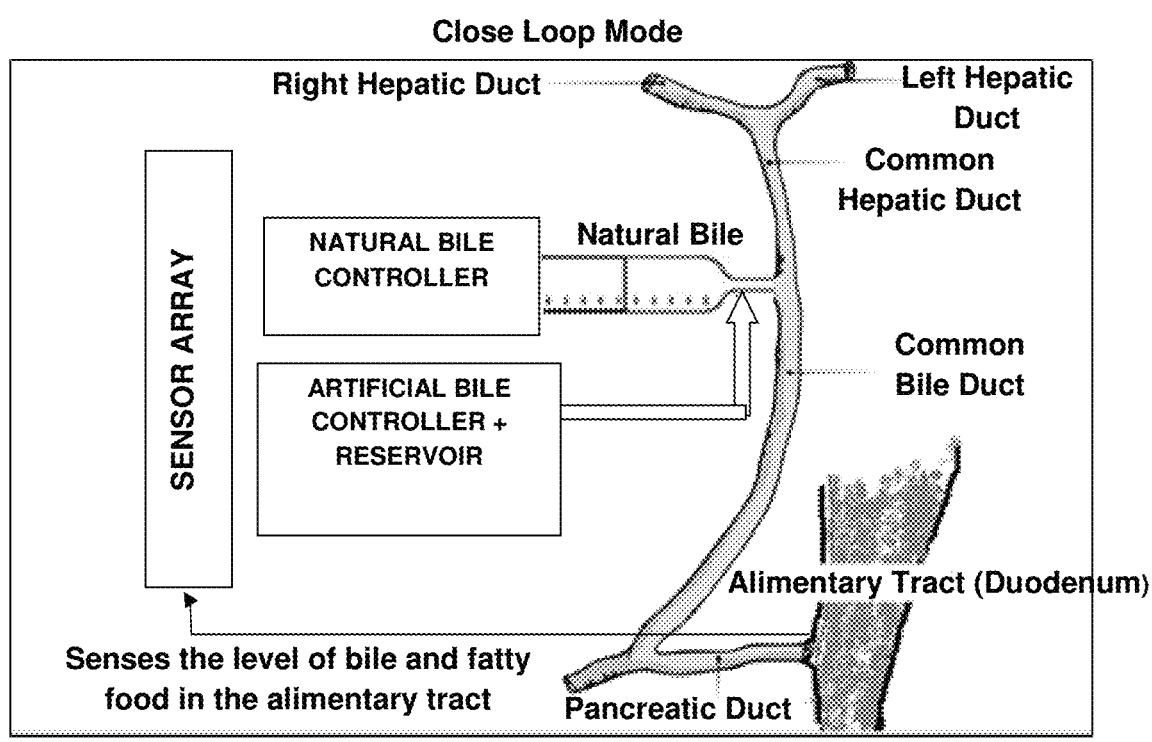

Referring to FIG. 4A-4C illustrates working of the device 108 into two modes i.e., an open loop mode and close loop mode for injecting the injectable amount of the bile into the alimentary tract of the patient. In the open loop mode (as shown in FIG. 4A & 4B), the device 108 may comprise a syringe and an implantable infusible pump. The syringe, with minimal friction may be introduced into the patient's body, will collect a third amount of bile (i.e., the natural bile) from the amount of bile secreted from the liver. The syringe may be further connected with the implantable infusion pump having an amount of artificial bile stored therein. Further, the device 108 may be further wirelessly connected with a handheld device. Through the handheld device, the user (doctor/surgeon) may input the amount of food taken by the patient. According to the embodiments of present disclosure, the handheld device may be the system 102 or the client device 104 (shown in FIG. 1) which determines the injectable amount of the bile required for the patient (as explained above). Thus, the handheld device may instruct the implantable infusion pump to inject the injectable amount of bile into the alimentary tract of the patient's body. Further, the device 108 working in the open loop mode may be mapped with FIGS. 3B and 3C in which the external computing device is the handheld device (as shown in FIG. 4A) which is required for instructing the implantable infusion pump for bile delivery.

In the close loop mode (4C), the device 108 may comprise the syringe, the implantable infusion pump, and a sensor array. In this approach also, the syringe (introduced into the patient's body) will collect the third amount of bile (i.e., the natural bile) from the amount of bile secreted and flow from the liver. Further, the syringe may be connected with the implantable infusion pump having the amount of artificial bile stored therein. In the closed loop approach, the syringe has a sensor array for detecting the positive feedback (stimulation) and the negative feedback (inhibition). The positive and the negative feedback were earlier explained in FIG. 3A. According to the embodiments of present disclosure, the syringe itself may be able to determine the bile-flow rate and the amount of fatty food. Further, the syringe having the sensor array may also determine the injectable amount of the bile based on the bile-flow rate and the amount of fatty food present in the alimentary tract. Further, the injectable amount of the bile may be injected in to the alimentary tract by the implantable infusion pump for providing the post-operative compensation in the patient's body. Further, the device 108 working in the close loop mode may be mapped with the FIG. 3D in which determining and injecting of the injectable amount of bile may be performed by single component only i.e., the implantable infusion pump of the device 108.

Figure 5:
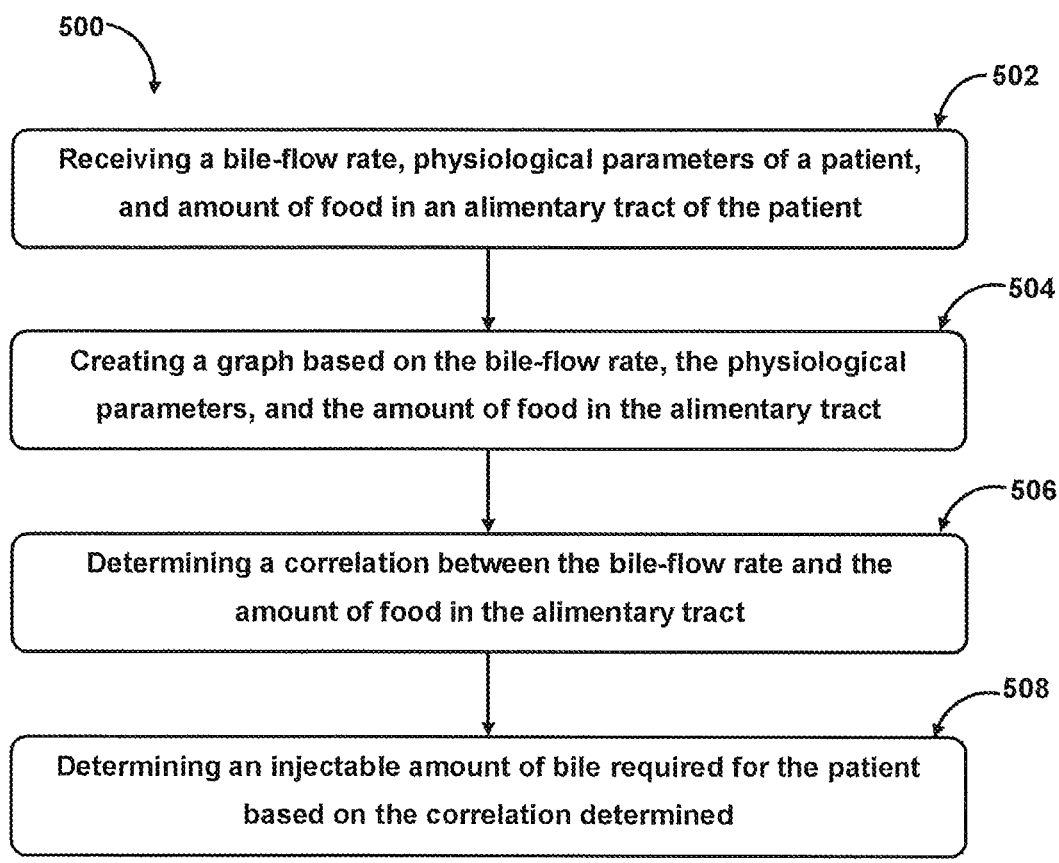
FIG. 5 illustrates a method for determining an injectable amount of bile required for a patient after gallbladder removal, in accordance with an embodiment of the present disclosure.

Referring now to FIG. 5, the method of determining an injectable amount of bile required for a patient after gallbladder removal is shown, in accordance with an embodiment of the present subject matter. The method 500 may be described in the general context of computer executable instructions. Generally, computer executable instructions can include routines, programs, objects, components, data structures, procedures, modules, functions, etc., that perform particular functions or implement particular abstract data types. The method 500 may also be practiced in a distributed computing environment where functions are performed by remote processing devices that are linked through a communications network. In a distributed computing environment, computer executable instructions may be located in both local and remote computer storage media, including memory storage devices.

The order in which the method 500 is described is not intended to be construed as a limitation, and any number of the described method blocks can be combined in any order to implement the method 500 or alternate methods. Additionally, individual blocks may be deleted from the method 500 without departing from the spirit and scope of the subject matter described herein. Furthermore, the method can be implemented in any suitable hardware, software, firmware, or combination thereof. However, for ease of explanation, in the embodiments described below, the method 500 may be considered to be implemented in the above described system 102.

At block 502, a bile-flow rate, physiological parameters of a patient and amount of food in an alimentary tract of the patient may be received. The bile-flow rate may indicate a first amount of bile delivered from gallbladder to the alimentary tract prior to the gallbladder removal and the physiological parameters may comprise age, sex, race, ethnicity, height, and weight of the patient.

At block 504, a graph may be created based on the bile-flow rate, the physiological parameters, and the amount of food in the alimentary tract At block 506, a correlation between the bile-flow rate and the amount of food in the alimentary tract may be determined.

At block 508, an injectable amount of bile required may be determined for the patient based on the correlation.

Although implementations for methods and systems for determining an injectable amount of bile have been described in language specific to structural features and/or methods, it is to be understood that the appended claims are not necessarily limited to the specific features or methods described. Rather, the specific features and methods are disclosed as examples of implementations for determining an injectable amount of bile required for the patient after gallbladder removal.

What is claimed is:

1. A method for injecting an injectable amount of bile required for a patient after gallbladder removal, the method comprising:
   receiving, by a processor, a first set of data and a second set of data associated to the patient, wherein the first set of data is received prior to the gallbladder removal from the patient and the second set of data is received after the gallbladder removal from the patient, and wherein the first set of data and the second set of data comprises a bile-flow rate, physiological parameters of the patient, and amount of food in an alimentary tract of the patient and wherein the physiological parameters comprise age, sex, race, ethnicity, height, and weight of the patient;
   creating, by the processor, a graph based on the first set of data and the second set of data; determining, by the processor, a correlation between the bile-flow rate and the amount of food in the alimentary tract prior to the gallbladder removal and after the gallbladder removal;
   determining, by the processor, the injectable amount of bile required for the patient based on the determined correlations; and injecting, by an implantable infusion pump, the injectable amount of bile into the alimentary tract of the patient's body, wherein the implantable infusion pump is communicatively coupled with the processor.

2. The method of claim 1, further comprising receiving a liver data, wherein the liver data indicates an amount of bile produced and secreted by the liver of the patient.

3. The method of claim 2, further comprising determining a second amount of bile based on the liver data, wherein the second amount of bile indicates a reserve amount of the bile present in the biliary tract of the patient.

4. The method of claim 2, further comprising providing post-operative compensation of bile for the patient, wherein the method comprising:
- collecting, by a syringe introduced in the patient's body, a third amount of bile from the amount of bile secreted by the liver of the patient, wherein the syringe is connected with an implantable infusion pump having an amount of artificial bile stored therein, and
- injecting, through the implantable infusion pump, the determined injectable amount of bile from the stored artificial bile into the alimentary tract for providing the post-operative compensation of the bile.

5. The method of claim 1, wherein the graph comprises a first curve corresponding to the first data set, and a second curve corresponding to the second data set, wherein the first curve indicates the correlation of the bile-flow rate and the amount of food in the alimentary tract for the first data set, and the second curve indicates the correlation of the bile-flow rate and the amount of food in the alimentary tract for the second data set.

6. The method of claim 1, wherein the bile-flow rate is measured using measuring techniques comprising one or more of an endoscopic retrograde cholangio-pancreatography (ERCP), a computerized tomography (CT), a magnetic resonance imaging (MRI), a flow Doppler, and a radio labeling.

7. A system for determining an injectable amount of bile required for a patient after gallbladder removal, wherein the system comprises:
- a processor;
- a memory coupled with the processor, wherein the processor executes a plurality of instructions, stored in the memory, when executed causes the processor to:
  - receive a first set of data and a second set of data associated to the patient, wherein the first set of data is received prior to the gallbladder removal from the patient and the second set of data is received after the gallbladder removal from the patient, and wherein the first set of data and the second set of data comprises a bile-flow rate, physiological parameters of the patient, and amount of food in an alimentary tract of the patient, and wherein the physiological parameters comprise age, sex, race, ethnicity, height, and weight of the patient;
  - create a graph based on the first set of data and the second set of data;
  - determine
    - a correlation between the bile-flow rate and the amount of food in the alimentary tract prior to the gallbladder removal and after the gallbladder removal, and
    - an injectable amount of bile required for the patient based on the determined correlations: and
  - inject by an implantable infusion pump the injectable amount of bile into the alimentary tract of the patient's body, wherein the implantable infusion pump is communicatively coupled with the processor.

8. The system of claim 7, wherein the processor further receives a liver data, wherein the liver data indicates an amount of bile produced and secreted by the liver of the patient.

9. The system of claim 8, wherein the processor further determines a second amount of bile based on the liver data, wherein the second amount of bile indicates a reserve amount of the bile present in the biliary tract of the patient.

10. The system of claim 8. further connected to a device comprising a syringe and the implantable infusion pump to provide post-operative compensation of bile for the patient, wherein
- the syringe, introduced into the patient's body, to collect a third amount of bile from the amount of bile secreted by the liver of the patient, wherein the syringe is connected with
- the implantable infusion pump having an amount of artificial bile stored therein; and
- the implantable infusion pump injects the injectable amount of bile from the stored artificial bile into the alimentary tract for providing the post-operative compensation of the bile.

11. The system of claim 7, wherein the graph comprises a first curve corresponding to the first data set and a second curve corresponding to the second data set, wherein the first curve indicates the correlation of the bile-flow rate and the amount of food in the alimentary tract for the first data set, and the second curve indicates the correlation of the bile-flow rate and the amount of food in the alimentary tract for the second data set.

* * * * *